(12) United States Patent
Hosaka et al.

(10) Patent No.: US 10,168,308 B2
(45) Date of Patent: Jan. 1, 2019

(54) ANALYSIS DEVICE

(71) Applicant: FRONTIER LABORATORIES LTD., Koriyama-shi, Fukushima (JP)

(72) Inventors: Akihiko Hosaka, Fukushima (JP); Atsushi Watanabe, Fukushima (JP); Chuichi Watanabe, Fukushima (JP)

(73) Assignee: FRONTIER LABORATORIES LTD., Koriyama-Shi (JP)

( * ) Notice: Subject to any disclaimer, the term of this patent is extended or adjusted under 35 U.S.C. 154(b) by 26 days.

(21) Appl. No.: 15/656,835

(22) Filed: Jul. 21, 2017

(65) Prior Publication Data

US 2018/0052143 A1 Feb. 22, 2018

(30) Foreign Application Priority Data

Aug. 16, 2016 (JP) ................................. 2016-159733
Jul. 5, 2017 (JP) ................................. 2017-131784

(51) Int. Cl.
*G01N 1/00* (2006.01)
*G01N 33/00* (2006.01)
*G01N 30/06* (2006.01)
*G01N 30/72* (2006.01)
G01N 30/02 (2006.01)

(52) U.S. Cl.
CPC ......... *G01N 33/0021* (2013.01); *G01N 30/06* (2013.01); *G01N 30/7206* (2013.01); *G01N 33/0013* (2013.01); *G01N 33/0016* (2013.01); G01N 2030/025 (2013.01); G01N 2030/067 (2013.01)

(58) Field of Classification Search
CPC ........... G01N 33/0021; G01N 33/0016; G01N 30/7206; G01N 30/06; G01N 33/0013; G01N 2030/025; G01N 2030/067
See application file for complete search history.

(56) References Cited

U.S. PATENT DOCUMENTS

2007/0009385 A1* 1/2007 Watanabe ............ G01N 17/004
422/68.1

OTHER PUBLICATIONS

Murata, Bunseki Kagaku, vol. 35 (1986), pp. 339-343, Discussed in specification, partial English translation, 5 pages.
R. Kinoshita et al., "The Optimization of the TG/DTA-MS Measurements and the Application for the Material Analysis", J. Mass Spectrom, Soc. Jpn., vol. 46, No. 4, 1998, pp. 365-373, Discussed in specification, English abstract, 9 pages.
Al Shiono et al., "Thermoanalytical characterization of polymers: A comparative study between thermogravimetry and evolved gas analysis using a temperature-programmable pyrolyzer", Polymer Testing 42 (2015), pp. 54-61, 8 pages.

* cited by examiner

*Primary Examiner* — Jyoti Nagpaul
(74) *Attorney, Agent, or Firm* — Rankin, Hill & Clark LLP

(57) ABSTRACT

Provided is an analysis device capable of obtaining sufficient sensitivity to a gas phase component, which is the analysis target, by a mass spectrometer even when a reactive gas is used as a carrier gas in evolved gas analysis. An analysis device 1 includes a heating device 3, a first carrier gas introduction device 4, a connecting conduit 5, a capillary tube 6, an oven 2, a mass spectrometer 7, and a second carrier gas introduction device 8. The second carrier gas introduction device 8 is configured to introduce helium, hydrogen and/or nitrogen into the connecting conduit 5.

5 Claims, 6 Drawing Sheets

ANALYSIS DEVICE

BACKGROUND OF THE INVENTION

Field of the Invention

The present invention relates to an analysis device.

Description of the Related Art

Conventionally, evolved gas analysis (EGA) is a known analysis method in which a sample is heated at a predetermined temperature, or heated under predetermined increasing temperature conditions, and the evolved gas phase components are introduced into a mass spectrometer via a capillary tube whose inner surface has only been deactivated and does not have any separating ability for analysis. Evolved gas analysis enables to know a relationship between a gas phase component and the temperature at which that gas phase component evolved. For example, it is able to know the temperature at which a side chain leaves a polymer component or the temperature at the like at which a main chain starts to decompose.

Normally, in gas chromatography, a separation column is used in which the inner surface of the capillary tube has been coated with a stationary phase liquid to give the separation column a separating ability, and hence helium, hydrogen or nitrogen, which do not cause the stationary phase liquid to degrade as a result of oxidation and the like, is used as carrier gas. Further, similar to gas chromatography, helium is also used as the carrier gas in evolved gas analysis (refer to Murata, BUNSEKI KAGAKU, 35 (1986) 339, R. Kinoshita et al., J. Mass Spectrom. Soc. Jpn., 46 (4) (1998) 365.). However, because the above-mentioned stationary phase liquid is not coated on the capillary tube used in evolved gas analysis, gases other than helium, hydrogen and nitrogen may be used as the carrier gas.

Therefore, in evolved gas analysis, gas that is directly, or via a catalyst, reactive with a first gas phase component evolved from the sample, for example, hydrogen, air, oxygen, carbon monoxide, carbon dioxide, methane, ethane, ethylene, and the like may be used. In evolved gas analysis, using gas that is reactive with the first gas phase component as a carrier gas (hereinafter, sometimes abbreviated as "reactive gas") enables to know a second gas phase component, which is a reaction product between the first gas phase component and the reactive gas, and also enables to know the temperature at which the second gas phase component evolved.

SUMMARY OF THE INVENTION

However, when a reactive gas is used in evolved gas analysis, there is a drawback in that the sensitivity of the mass spectrometer to the second gas phase component, which is the analysis target, decreases by a factor rate of about several dozen to several hundred.

The present invention solves this drawback, and it is an object of the present invention to provide an analysis device capable of obtaining sufficient sensitivity to a second gas phase component, which is the analysis target, by a mass spectrometer even when a reactive gas is used in the evolved gas analysis.

The analysis device according to the present invention includes: a heating device configured to produce a first gas phase component by heating a sample including organic matter; a first carrier gas introduction device configured to introduce into the heating device a first carrier gas consisting of gas that is directly, or via a catalyst, reactive with the first gas phase component; a connecting conduit into which the first carrier gas including a second gas phase component as a reaction product between the first gas phase component and the first carrier gas is introduced; a capillary tube which is connected to the connecting conduit and which is capable of being used in evolved gas analysis; an oven configured to house the capillary tube; a mass spectrometer connected to the capillary tube at outside of the oven; and a second carrier gas introduction device configured to introduce into the connecting conduit at least one kind of gas selected from helium, hydrogen and nitrogen as a second carrier gas.

According to the analysis device of the present invention, the second gas phase component is produced as a reaction product between the first carrier gas and the first gas phase component that evolves from the organic matter included in the sample when the sample is heated by the heating device under a first carrier gas atmosphere introduced from the first carrier gas introduction device. The second gas phase component is introduced into the capillary tube via the connecting conduit by the first carrier gas.

As the capillary tube, any capillary tube capable of being used in evolved gas analysis can be used. The capillary tube may be a capillary tube whose inner surface has only been deactivated and that does not have any separating ability, or may be a capillary tube that does have a separating ability, but has been coated with a polymer of a few μm or less. The second gas phase component introduced into the capillary tube is introduced into the mass spectrometer and analyzed essentially without being separated. During this process, because the oven is heated to a temperature of 200° C. or more, and the capillary tube is housed in the oven, the second gas phase component is introduced into the mass spectrometer without condensing inside the capillary tube.

In the mass spectrometer, although the second gas phase component is ionized by the ion source, the first carrier gas is also simultaneously ionized at this point. If the intensity of the ions generated by the ionization of the first carrier gas is too strong, the ionization efficiency of the second gas phase component may decrease, and the sensitivity of the mass spectrometer to the second gas phase component may deteriorate.

Therefore, in the analysis device according to the present invention, the second carrier gas is introduced into the connecting conduit from the second carrier gas introduction device. The second carrier gas consists of at least one kind of gas selected from helium, hydrogen and nitrogen, and is not ionized by the ion source of the mass spectrometer. As the second carrier gas, either helium, hydrogen or nitrogen may be used alone, or a mixture of helium, hydrogen and nitrogen may be used.

As a result, according to the analysis device of the present invention, the first carrier gas is diluted with the second carrier gas, the ionization efficiency of the second gas phase component is relatively improved, and a sufficient sensitivity to the second gas phase component can be obtained by the mass spectrometer.

In the analysis device according to the present invention, examples of gases that may be used as the first carrier gas include at least one kind of gas selected from a group consisting of hydrogen, air, oxygen, carbon monoxide, carbon dioxide, methane, ethane, and ethylene. As the first carrier gas, each of the above-mentioned gases may be used independently or two or more kinds may be used in combination.

Further, it is preferred that the analysis device according to the present invention include in the connecting conduit a split vent tube configured to adjust the amount of gas to be introduced into the capillary tube by discharging a part of the gas introduced into the connecting conduit. By including the split vent tube, the analysis device according to the present invention can discharge a part of the first and second carrier gases and the second gas phase component that have been introduced into the connecting conduit. As a result, the effect of the dilution of the first carrier gas with the second carrier gas is further improved, and even better sensitivity to the gas phase component evolved from the organic matter can be achieved by the mass spectrometer.

In addition, for the analysis device according to the present invention, it is preferred that the amount of the second carrier gas introduced by the second carrier gas introduction device be in a range of 2 to 500 times the amount of the first carrier gas introduced by the first carrier gas introduction device, and more preferably be an amount in the range of 5 to 60 times. By setting the amount of the second carrier gas introduced by the second carrier gas introduction device to be in the above-mentioned range with respect to the amount of the first carrier gas introduced by the first carrier gas introduction device, the analysis device according to the present invention is capable of reliably diluting the first carrier gas with the second carrier gas, and obtaining excellent sensitivity by the mass spectrometer to the gas phase component evolved from the organic matter.

DETAILED DESCRIPTION OF THE PREFERRED EMBODIMENTS

Next, an embodiment of the present invention is described in more detail with reference to the attached drawings.

Figure 1:
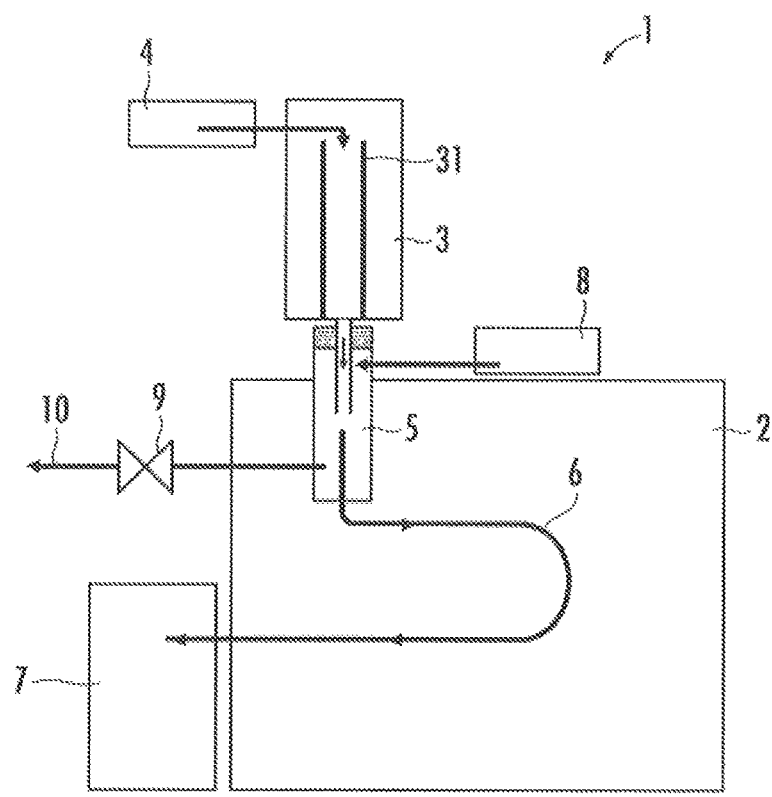
FIG. 1 is a system configuration diagram illustrating a configuration of an analysis device according to the present invention.

As illustrated in FIG. 1, an analysis device 1 according to the present embodiment includes a heating device 3 erected at an outside of an oven 2, a first carrier gas introduction device 4 configured to introduce a first carrier gas to an upper portion of the heating device 3, a connecting conduit 5 provided at a lower portion of the heating device 3, a capillary tube 6 that is housed in the oven 2 and that has one end connected to the connecting conduit 5, a mass spectrometer 7 connected to the other end of the capillary tube 6 at an outside of the oven 2, and a second carrier gas introduction device 8 configured to introduce a second carrier gas into the connecting conduit 5. Further, the analysis device 1 also includes a split vent tube 10 connected to the connecting conduit 5 via an on-off valve 9.

In the analysis device 1, the interior of the oven 2 can be held at a predetermined temperature, for example, a temperature of 200 to 350° C. The heating device 3 includes a quartz tube 31 and a heater for heating (not shown) that is arranged on an outer circumferential side of the quartz tube 31. The heating device 3 is configured to cause a first gas phase component to evolve from organic matter contained in a sample that has been charged into the quartz tube 31 by heating the sample to a predetermined temperature, or by heating the sample under predetermined increasing temperature conditions, for example, an increasing temperature program in which the temperature is increased from 50° C. to 800° C. at a rate of 20° C. per minute.

The first carrier gas introduction device 4 is configured to introduce a first carrier gas consisting of gas that is directly, or via a catalyst, reactive with the first gas phase component into the heating device 3 at a predetermined flow rate. Examples of gases that may be used as the first carrier gas include at least one kind of gas selected from the group consisting of hydrogen, air, oxygen, carbon monoxide, carbon dioxide, methane, ethane, and ethylene.

As the capillary tube 6, any capillary tube capable of being used in evolved gas analysis can be used. The capillary tube 6 may be a capillary tube whose inner surface has only been deactivated, and that does not have any separating ability, or may be a capillary tube that does have a separating ability, but only has been coated with a polymer of a few μm or less. The capillary tube 6 is, for example, a stainless steel tube having an inner diameter of 0.15 mm, an outer diameter of 0.47 mm, and a length of 2.5 m. A capillary tube whose inner surface has only been deactivated, that is not coated with a stationary phase liquid, and that does not have a separating ability, may be used.

The mass spectrometer 7 includes a sample introduction unit to which the capillary tube 6 is connected, an ion source configured to ionize the sample by applying a charge, an analysis unit configured to separate the ionized sample for each mass-to-charge ratio (m/z), a detection unit configured to detect an intensity of the sample separated by the analysis unit for each mass-to-charge ratio (m/z), and a data processing unit configured to create a mass spectrum from the data obtained by the detection unit. As the ion source, for example, an electron ionization method in which the sample is ionized by causing thermal electrons emitted from a rhenium-tungsten filament to collide with the sample, may be used. Further, the analysis unit is configured to separate the ionized sample for each mass-to-charge ratio (m/z) by using a magnetic field deflection type, quadrupole type, or similar type methods.

Further, the second carrier gas introduction device 8 is configured to introduce at least one kind of gas selected from helium, hydrogen and nitrogen as the second career gas into the connecting conduit 5 at a predetermined flow rate.

Next, operation of the analysis device 1 according to the present embodiment is described.

In the analysis device 1 of the present embodiment, the first carrier gas is introduced into the quartz tube 31 of the heating device 3 at a predetermined flow rate from the first carrier gas introduction device 4. Further, the sample including organic matter is charged into the quartz tube 31, and heated to a predetermined temperature or heated under predetermined increasing temperature conditions. As a result, a second gas phase component is obtained, as a direct reaction product or as a reaction product via a catalyst, between the first carrier gas and the first gas phase component evolved from the heating of the organic component under a first carrier gas atmosphere. The second gas phase component is introduced into the connecting conduit 5 by the first carrier gas.

In the connecting conduit 5, the second carrier gas is introduced from the second carrier gas introduction device 8 at a predetermined flow rate, and the first carrier gas is diluted with the second carrier gas. At this stage, it is preferred that the second carrier gas be introduced at a flow rate in the range of 2 to 500 times that of the first carrier gas, and more preferably at a flow rate in the range of 5 to 60 times that of the first carrier gas. As a result, the first carrier gas is diluted with the second carrier gas by a factor (magnification) in the range of preferably 2 to 500, and more preferably by a factor (magnification) in the range of 5 to 60.

By introducing the second carrier gas in this manner, the amount of gas introduced from the connecting conduit 5 to the capillary tube 6 is a larger amount than necessary. Here, this gas is composed of the second gas phase component and the first carrier gas diluted with the second carrier gas. Therefore, by opening the on-off valve 9, for example, 80% or more of the gas in the connecting conduit 5 is discharged from the split vent tube 10, and the remaining gas is introduced into the capillary tube 6.

Next, the gas is introduced into the ion source via the sample introduction unit of the mass spectrometer 7, and the second gas phase component is ionized. Although the first carrier gas is also simultaneously ionized at this point, because the first carrier gas is diluted with the second carrier gas, which is not ionized, the intensity of the ions generated from the first carrier gas is low enough that interference with the detection by the detection unit of the second gas phase component ions can be kept to a minimum.

Figure 2:
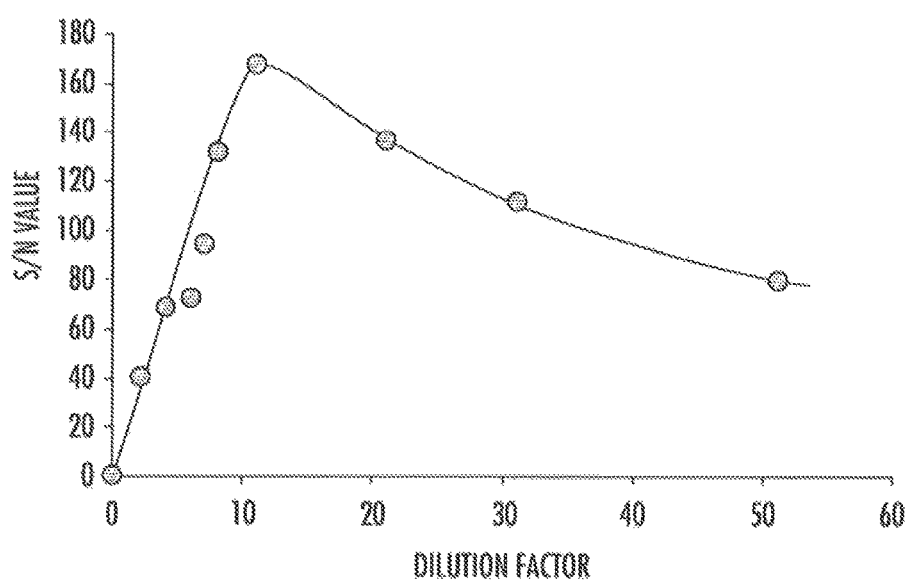
FIG. 2 is a graph showing a relationship between a dilution factor (magnification rate) of a second carrier gas with respect to a first carrier gas and an S/N value as an index of sensitivity to a second gas phase component by a mass spectrometer.

FIG. 2 shows a relationship in the analysis device 1 of the present embodiment between a dilution factor when the first carrier gas has been diluted with the second carrier gas and an S/N value of the second gas phase component detected by the detection unit. The S/N value is a ratio of a signal level S to a noise level N for the ions of the second gas phase component detected by the detection unit. The larger the S/N value, the better the sensitivity to the ions of that gas phase component.

From FIG. 2, it can be seen that with the analysis device 1 of the present embodiment, for a dilution factor of about 2, the S/N value is 40 and a good sensitivity is obtained, and for a dilution factor of about 10, the S/N value is very large. Further, in FIG. 2, when the dilution factor is larger than 60, it can be confirmed by drawing a line of approximation of the S/N value to the dilution factor that the S/N value is about 40 even when the dilution factor is 500.

Therefore, with the analysis device 1 of the present embodiment, from the perspective of obtaining an S/N value of about 40, it is preferred that the dilution factor be in the range of 2 to 500, and from the perspective of obtaining an S/N value of 70 or more, it is more preferred that the dilution factor be in the range of 5 to 60.

Further, with the analysis device 1 of the present embodiment, because the first carrier gas is diluted in the manner described above, when the ion source of the mass spectrometer 7 includes a rhenium-tungsten filament, the effect of a decrease in deterioration of the filament by the first carrier gas can also be obtained.

Next, an example and a comparative example of the present invention are illustrated.

Example 1

In this example, while air was introduced as the first carrier gas at a flow rate of 10 mL/min from the first carrier gas introduction device 4 into the heating device 3, 25 μg of polystyrene as the sample was charged into the quartz tube 31 of the analysis device 1, and heated under conditions in which the temperature was increased from 100° C. to 600° C. at a rate of 20° C./min to cause a gas phase component to evolve as a reaction product between the polystyrene and oxygen in the air. Further, helium was introduced as the second carrier gas at a flow rate of 100 mL/min from the second carrier gas introduction device 8 into the connecting conduit 5, 99% of the gas in the connecting conduit 5 was discharged from the split vent tube 10, the remaining gas was introduced into the mass spectrometer 7 via the capillary tube 6, and evolved gas analysis was carried out.

Figure 3:
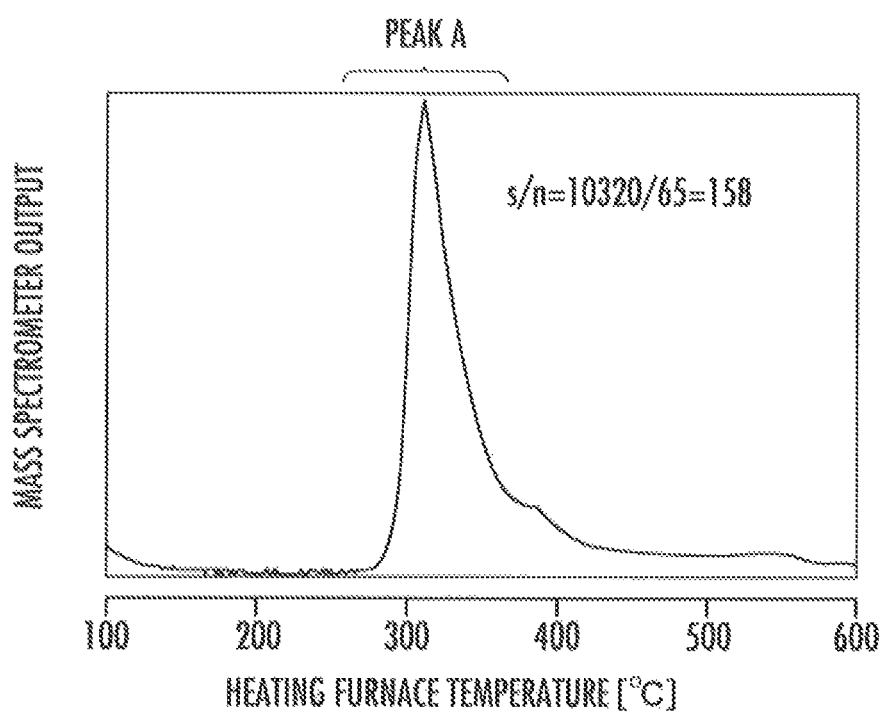
FIG. 3 is an EGA curve (TIC mode) measured using the analysis device according to the present invention in Example 1.
Figure 4:
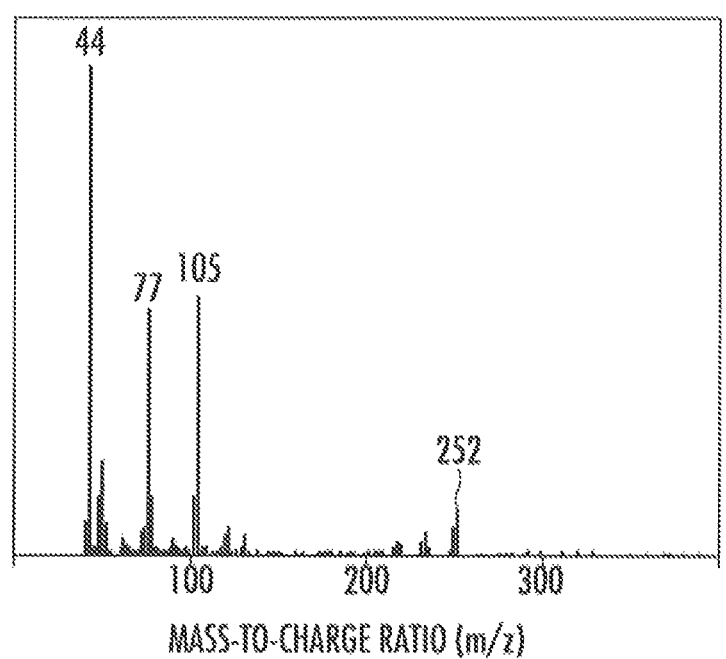
FIG. 4 is a mass spectrum obtained from the EGA curve (TIC mode) of FIG. 3.

The obtained EGA curve (TIC mode) is shown in FIG. 3. Further, a mass spectrum obtained from the EGA curve (TIC mode) of FIG. 3 is shown in FIG. 4.

As shown in FIG. 3, for the EGA curve (TIC mode) obtained in Example 1, at a peak A the noise level (N) was 65, the signal level (S) was 10,320, and hence the S/N value was 158. Further, from FIG. 4, it can be seen that acetaldehyde (m/z=44), benzaldehyde (m/z=105), and the like were detected as the reaction products between the polystyrene and the oxygen in the air.

Comparative Example 1

In this comparative example, evolved gas analysis was carried out in exactly the same manner as Example 1, except that none of the second carrier gas was introduced from the second carrier gas introduction device 8 into the connecting conduit 5.

Figure 5:
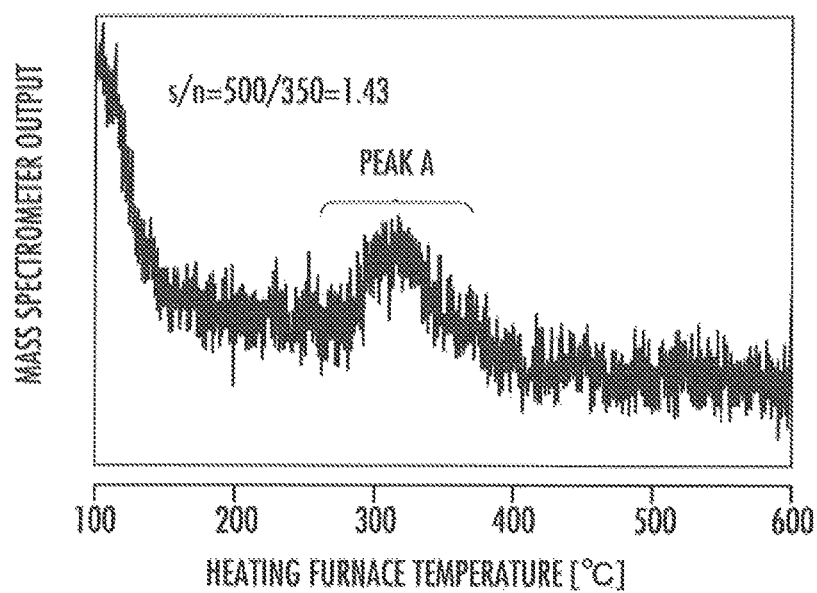
FIG. 5 is an EGA curve (TIC mode) measured using the analysis device according to the present invention in Comparative Example 1.
Figure 6:
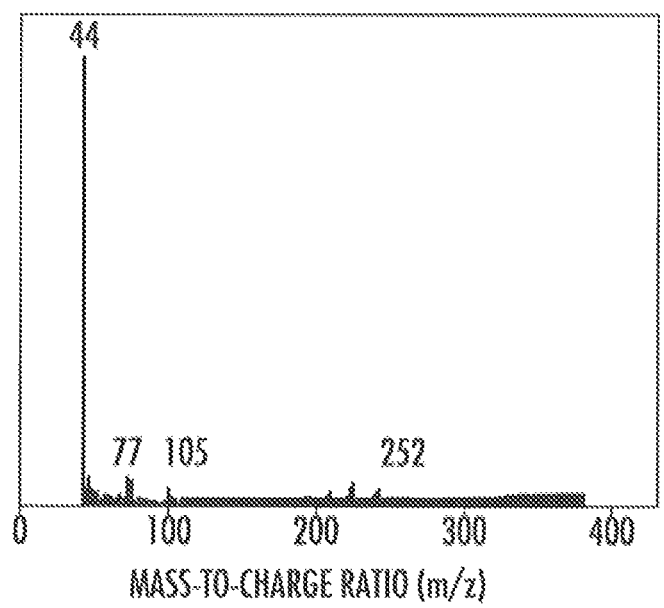
FIG. 6 is a mass spectrum obtained from the EGA curve (TIC mode) of FIG. 5.

The obtained EGA curve (TIC mode) is shown in FIG. 5. Further, a mass spectrum obtained from the EGA curve (TIC mode) of FIG. 5 is shown in FIG. 6.

As shown in FIG. 5, for the EGA curve (TIC mode) obtained in Comparative Example 1, at the peak A the noise level (N) was 350, the signal level (S) was 500, and hence the S/N value was just 1.43. Further, from FIG. 6, it can be seen that a tiny amount of cleaved ions such as acetaldehyde (m/z=44) and benzaldehyde (m/z=77, 105) were detected as gas phase components evolved by the heating of the polystyrene under an air atmosphere.

Thus, according to the analysis device 1 (Example 1) of the present embodiment, the S/N value is 100 times or more greater than when none of the second carrier gas was introduced into the connecting conduit 5 (Comparative Example 1), and also from the mass spectrum results, it is clear that a good sensitivity to the gas phase components evolved from the organic matter can be obtained.

What is claimed is:

1. An analysis device comprising:
   a heating device configured to produce a first gas phase component by heating a sample including organic compounds;
   a first carrier gas introduction device connected to an upstream portion of the heating device and configured to introduce into the heating device a first carrier gas consisting of gas that is directly, or via a catalyst, reactive with the first gas phase component;
   a connecting conduit connected to a downstream portion of the heating device, and the first carrier gas including a second gas phase component as a reaction product between the first gas phase component and the first carrier gas, is introduced into the connecting conduit;
   a capillary tube which is connected to the connecting conduit and which is capable of being used in evolved gas analysis;
   an oven configured to house the capillary tube;

a mass spectrometer connected to the capillary tube at outside of the oven; and a second carrier gas introduction device configured to introduce into the connecting conduit at least one kind of gas selected from helium, hydrogen and nitrogen as a second carrier gas.

2. The analysis device according to claim 1, wherein the first carrier gas is at least one kind of gas selected from a group consisting of hydrogen, air, nitrogen, oxygen, carbon monoxide, carbon dioxide, methane, ethane, and ethylene.

3. The analysis device according to claim 1, wherein the connecting conduit comprises a split vent tube configured to adjust an amount of gas to be introduced into the capillary tube by discharging a part of the gas introduced into the connecting conduit.

4. The analysis device according to claim 1, wherein an amount of the second carrier gas introduced by the second carrier gas introduction device is in a range of 2 to 500 times an amount of the first carrier gas introduced by the first carrier gas introduction device.

5. The analysis device according to claim 1, wherein an amount of the second carrier gas introduced by the second carrier gas introduction device is in a range of 5 to 60 times an amount of the first carrier gas introduced by the first carrier gas introduction device.

\* \* \* \* \*